United States Patent [19]

Schumacher et al.

[11] Patent Number: 4,873,335
[45] Date of Patent: Oct. 10, 1989

[54] 3-PHENETHYL-2-BENZENE-AMIDES OR AZA-DERIVATIVES THEREOF

[75] Inventors: Doris P. Schumacher, Florham Park; Bruce L. Murphy, Elizabeth; Jon E. Clark, Highland Park, all of N.J.

[73] Assignee: Schering Corporation, Kenilworth, N.J.

[21] Appl. No.: 127,743

[22] Filed: Dec. 2, 1987

Related U.S. Application Data

[60] Division of Ser. No. 839,016, Mar. 12, 1986, Pat. No. 4,731,447, which is a continuation-in-part of Ser. No. 733,428, May 13, 1985, abandoned.

[51] Int. Cl.⁴ ............... C07D 213/56; C07C 103/22; C07C 103/26
[52] U.S. Cl. .................. 546/194; 546/316; 546/323; 564/161; 564/166; 564/171; 564/184; 564/185; 564/186
[58] Field of Search ............... 546/316, 323, 194; 564/161, 166, 171, 184, 185, 186

[56] References Cited

U.S. PATENT DOCUMENTS

| | | | |
|---|---|---|---|
| 3,326,924 | 6/1967 | Villani et al. | 546/93 |
| 3,357,986 | 1/1967 | Villani | 546/93 |
| 3,366,635 | 1/1968 | Villani | 546/93 |
| 3,419,565 | 12/1986 | Villani | 546/93 |
| 3,717,647 | 2/1973 | Villani et al. | 546/93 |
| 4,659,716 | 4/1987 | Villani et al. | 514/290 |

FOREIGN PATENT DOCUMENTS 1470314 4/1972 Fed. Rep. of Germany ........ 546/93
631095 1/1972 Japan ..................................... 546/93

OTHER PUBLICATIONS

Villani et al. J. Med. Chem. (1972), vol. 15 No. 7 pp. 750-754.
Fieser and Fieser, Reagents for Organic Synthesis, (John Wiley & Sons, Inc. (1967), pp. 396, 455 and 1219.
Daub et al., Org. Chem., vol. 38, No. 4, (1973), pp. 828-829.
Takayama et al., Heterocycles, vol. 9, No. 10, (1978) pp. 1429-1432.

*Primary Examiner*—John M. Ford
*Attorney, Agent, or Firm*—James R. Nelson; Henry C. Jeanette; Stephen I. Miller

[57] ABSTRACT

Compounds of the formula:

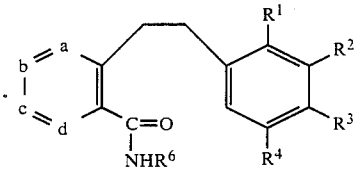

are produced, with the variables as indicated within.

7 Claims, No Drawings

3-PHENETHYL-2-BENZENE-AMIDES OR AZA-DERIVATIVES THEREOF

This application is a division of U.S. Application Ser. No. 839,016, filed on Mar. 12, 1986, now U.S. Pat. No. 4,731,447, which is a continuation-in-part of U.S. Application Ser. No. 733,428 filed on May 13, 1985, now abandoned.

BACKGROUND OF THE INVENTION

The present invention relates to a process for preparing piperidylidene dihydro-dibenzo[a,d]cycloheptenes or aza-derivatives thereof and intermediates and individual steps in such process.

Various process for preparing 1, 2, 3 or 4-aza-5-(4-piperidylidene)-10,11-dihydro-dibenzocycloheptene derivatives are disclosed in U.S. Pat. Nos. 3,326,924 and 3,717,647 and Villani et al., *Journal of Medicinal Chemistry*, 1972, Vol. 15, No. 7, pp. 750-754. For example, one such scheme is as follows:

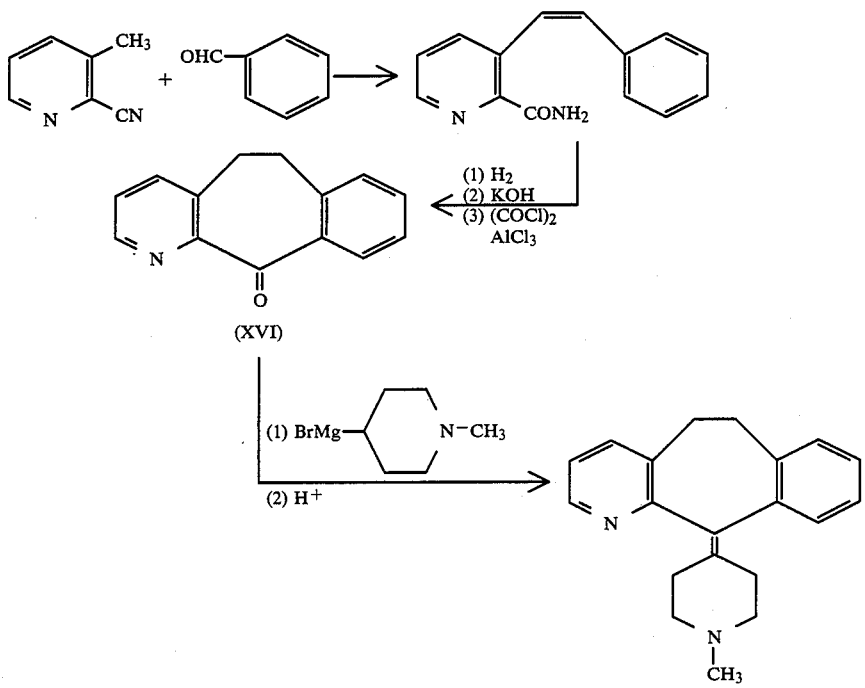

This type scheme has certain disadvantages in that the ring closure steps to the aza-ketone intermediate of formula XVI give relatively poor yields and are labor intensive steps. Also, the reaction of the Grignard reagent with the aza-ketone intermediate of formula XVI can proceed via an undesired 1,6 addition reducing the yield of the desired end product.

U.S. Pat. No. 3,326,924 also discloses other processes proceeding via, for example, 5,6-dihydro-11H-benzo[5,6]cvclohepta[1,2-b]pyridin-11-one as an azaketone intermediate in the preparation of, e.g., azatadine. In one such process, ethyl nicotinate is condensed with phenylacetonitrile to form a keto the keto nitrile with a strong mineral acid. Reduction of the so produced 3-pyridyl ketone to a 3-phenethyl pyridine may be carried out by the well-known Wolff-Kishner reaction. The phenethyl pyridine is transformed into its N-oxide by means of a peroxy acid. The N-oxide is then reacted with dimethyl sulfate and then aqueous sodium cyanide to produce a 3-phenethyl-2-pyridylnitrile. The nitrile is cyclized directly to the 5,6- dihydro-11H-benzo-[5,6]cyclohepta[1,2-b]pyridin-11-one. Although this prior art process operates successfully, it would be desirable to use a process which is more economical to provide the aza-ketone intermediate.

SUMMARY OF THE INVENTION

A process for preparing piperidylidene-dihydrodibenzo[a,d]cycloheptenes or aza-derivatives thereof of formula I

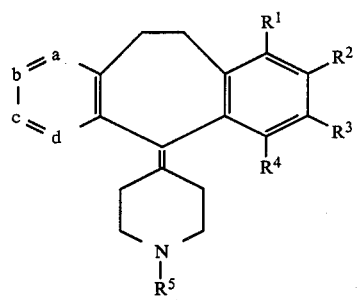

has now been found which results in a higher effective Yield of the desired end products in comparison to the processes described above. One aspect of the new process eliminates the labor intensive step of ring closure to a ketone intermediate (e.g., an aza-ketone), can eliminate the poor yielding Grignard reaction with the ketone intermediate, and reduces the total number of steps in the synthesis from six to five. Thus, a first process aspect of the invention involves a new process for preparing a compound of formula I comprising the steps of reacting a compound of formula II with a compound of formula III

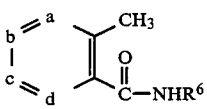

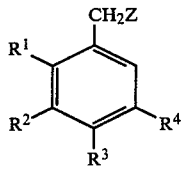

in the presence of base to produce a compound of formula IV

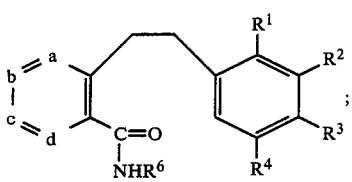

reacting the compound of formula IV with a dehydrating agent to produce a compound of formula V

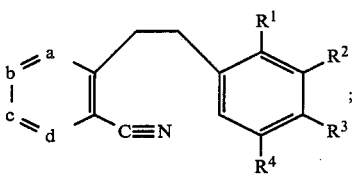

reacting the compound of formula V with a compound of formula VI

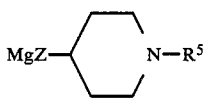

and hydrolyzing the product thereof to produce a compound of formula VII

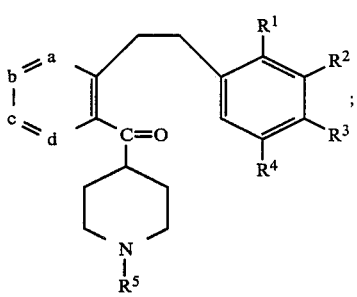

and reacting the compound of formula VII with a super acid having a Hammett acidity function of less than minus 12 to produce the compound of formula I, wherein:

a, b, c, and d represent CH or one of a, b, c and d represents N and the others represent CH;

$R^1$, $R^2$, $R^3$ and $R^4$ may be the same or different and each independently represents hydrogen, alkyl having from 1 to 6 carbon atoms, halo (i.e., fluoro, chloro, bromo or iodo), nitro, alkoxy having from 1 to 6 carbon atoms or trifluoromethyl;

$R^5$ represents an N-protecting group which does not prevent formation of the Grignard reagent of formula VI;

$R^6$ represents a protecting group that will protect the N of the group CONHR$^6$ in formula II from reaction with an alkylating agent such as a compound of formula III: and Z represents chloro, bromo or iodo. The compounds of formula I can be converted to the corresponding 1-substituted-4-piperidylidene and 4-piperidylidene derivatives, i.e., where the substituent on the piperidinyl nitrogen atom is COOR$^8$ wherein $R^8$ is as defined below or H.

A second process aspect of the invention includes a process which comprises reacting a compound of formula VIIa

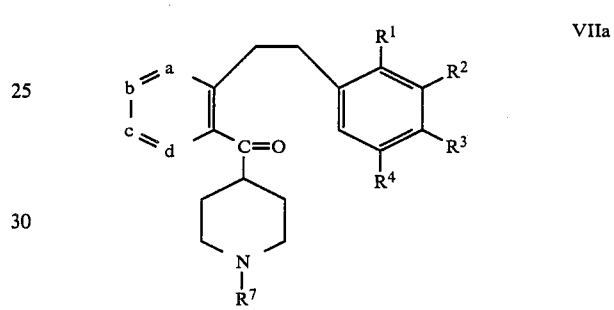

with a super acid having a Hammett acidity function value of less than minus 12 to produce a compound of formula Ia

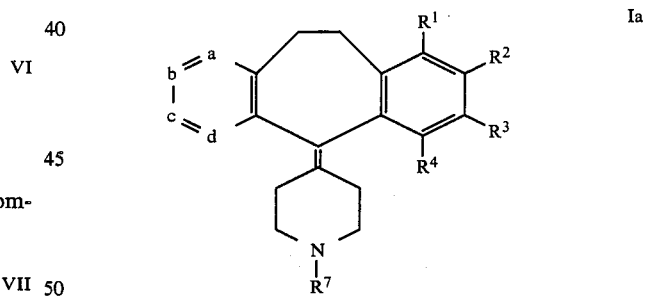

wherein a, b, c, d, $R^1$, $R^2$, $R^3$, and $R^4$ are as defined above and $R^7$ is an N-protecting group, -H or -COOR$^8$, wherein $R^8$ represents $C_1$ to $C_{12}$ alkyl, substituted $C_1$ to alkenyl, phenyl, substituted phenyl, $C_7$ to $C_{10}$ phenylalkyl or $C_7$ to $C_{10}$ phenylalkyl wherein the phenyl moiety is substituted, or $R^8$ is 2-, 3-, or 4-piperidyl or said substituted $C_1$ to $C_{12}$ alkyl and on said substituted $C_2$ to $C_{12}$ alkenyl are selected from amino or substituted amino and the substituents on said substituted amino are selected from $C_1$ to $C_6$ alkyl, the substituents on said substituted phenyl and on said substituted phenyl moiety of the $C_7$ to $C_{10}$ phenylalkyl are selected from $C_1$ to $C_4$ alkyl and halo, and the substituent on said N-substituted piperidyl is $C_1$ to $C_4$ alkyl.

A third process aspect of the invention involves a process for preparing an intermediate of formula XIII by reacting a compound of formula II

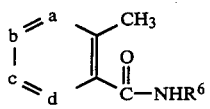

with a compound of formula III

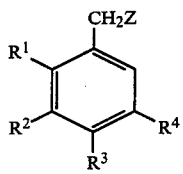

in the presence of base to produce a compound of formula IV

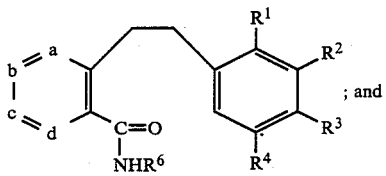

converting the compound of formula IV to a compound of formula XIII, wherein a, b, c, d, $R^1$, $R^2$, $R^3$, $R^4$, $R^6$ and Z are as defined above.

Still other aspects of the present invention comprise an intermediate of the formula IV

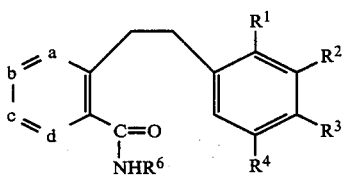

wherein a, b, c, d, $R^1$, $R^2$, $R^3$, $R^4$ and $R^6$ are as defined above, and an intermediate of the formula XV

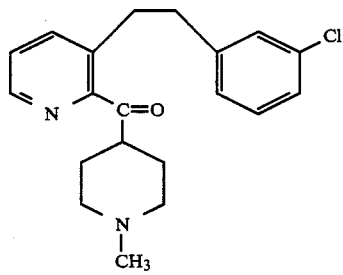

or a pharmaceutically acceptable salt thereof, preferably the hydrochloride salt.

The intermediates of formula IV are particularly useful in the preparation of the compounds of formula XIII, e.g., these intermediates provide improved yields of the compounds of formula XIII in the third process aspect of the invention above. The intermediates of formula IV also can be used to conveniently prepare the cyano compounds of formula V in the first process aspect of the invention as described above. The intermediate of formula XV has been found to provide particular advantage in the first and second process aspects of the invention in that such an intermediate allows easy separation from the reactants leading thereto and provides a high degree of purity. Thus, the ring closure step in these first and second process aspects can start with clean material, thus a purer ring-closed product.

The above described processes are preferably performed with compounds in which $R^2$ and $R^3$ are independently hydrogen or halo (such as chloro or fluoro); $R^1$ and $R^4$ are hydrogen; d is N; and a, b and c are CH. A preferred N-protecting $R^5$ group is methyl and a preferred $R^6$ group is tertiary butyl.

When utilized herein, the terms below have the following scope:

N-protecting group ($R^5$ or $R^7$) - represents any group which will allow reaction of magnesium with the 4-halo substituent of a 4-halo-substituted piperidinyl compound without reacting with other portions of the compound and which can later be removed.

a protecting group ($R^6$) - represents any group which will protect the N of the group $CONHR^6$ in the compound of formula II from reaction with an alkylating agent, e.g., an aralkyl halide such as a compound of formula III.

aryl (including the aryl portions of aralkyl)—represents a carbocyclic group containing from 6 to 15 carbon atoms and having at least one benzene ring. Preferably, aryl is phenyl or substituted phenyl (with the proviso that the substituent is not halo in the case of $R^5$). Suitable substituents may include alkoxy, alkyl, alkoxyalky, etc. Suitable aryl groups include phenyl, naphthyl, indenyl, indanyl, etc., with all appropriate points of attachment being intended.

alkyl (including the alkyl portions of alkoxy, aralkyl, etc.)—represents a straight or branched carbon chain containing from 1 to 6 carbon atoms.

DETAILED DESCRIPTION OF THE INVENTION

An appropriate starting material for the process of the invention is an appropriately substituted cyano-toluene or cyano-methyl pyridine (such as 2-cyanotoluene, 2-cyano-3-methyl-pyridine, 3-cyano-4-methyl-pyridine, 3-methyl-4-cyano-pyridine or 2-methyl-3-cyanopyridine). The cyano compound can be converted into the corresponding carboxylic acid, e.g, 3-methyl-2-pyridine carboxylic acid or activated esters thereof, e.g., a succinimide or hydroxysuccinimide ester, by reactions conventional in the art. The carboxylic acid or activated ester thereof can then be reacted with the appropriate amino compound of formula $NH_2R$ to formulate a compound of formula II

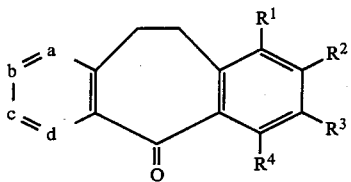

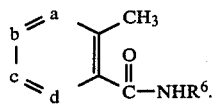

II $R^6$ is preferably a tertiary butyl group. A compound having such an $R^6$ tertiary butyl group can be obtained, for example, by a Ritter reaction in which a tertiary butyl compound is reacted with a cyano-toluene or cyano-methyl-pyridine compound to produce a compound of formula XVII

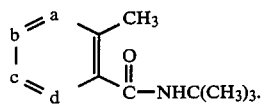

XVII

This reaction is generally performed in an acid such as concentrated sulfuric acid or concentrated sulfuric acid in glacial acetic acid. Suitable tertiary butyl compounds include, but are not limited to, t-butyl alcohol, t-butyl chloride, t-butyl bromide, t-butyl iodide, isobutylene or any other compound which under hydrolytic conditions forms t-butyl carboxamides with cyano compounds. The temperature of the reaction will vary depending on the reactants, but generally is conducted in the range of from about 50° to about 100° C. with t-butyl alcohol. The reaction may be performed with inert solvents but is usually run neat.

The compound formula II is reacted with an appropriate benzyl halide of formula III in the presence of a base to form the compound of formula IV above. Examples of appropriate benzyl halides include, but are not limited to, benzyl chloride, 3-chloro-benzyl chloride, 3-fluoro-benzyl chloride, 3,4-dichlorobenzylchloride, 4-fluoro-benzyl chloride, 3-nitro-benzyl chloride, 3-methyl-benzyl chloride, etc. Any suitable base can be employed, e.g., an alkyl lithium compound such as n-butyl lithium in tetrahydrofuran (THF). Preferably the base has a $pK_a$ of greater than 20 and more preferably greater than 30. This reaction can be conducted at any suitable temperature, e.g., temperatures of from about $-78°$ C. to about 30° C., preferably from about $-40°$ C. to about $-30°$ C.. The reaction can be performed in any suitable inert solvent such as THF, diethyl ether, etc.

The amide of formula IV is converted to the cyano compound of formula V by the use of a suitable dehydrating agent such as $POCl_3$, $SOCl_2$, $P_2O_5$, toluene sulfonyl chloride in pyridine, oxalyl chloride in pyridine, etc. This reaction can be performed in the absence of or with an inert co-solvent such as xylene. The dehydrating agent such as $POCl_3$ is employed in equivalent amounts or greater and preferably in amounts of from about 2 to about 15 equivalents. Any suitable temperature and time can be employed for performing the reaction, but generally heat is added to speed up the reaction. Preferably, the reaction is performed at or near reflux.

The cyano compound of formula V is reacted with a Grignard reagent (formula VI) prepared from the appropriate 1-(N-protected)-4-halopiperidine. Any suitable N-protecting group known in the art to protect the piperidinyl nitrogen atom from reaction during formation of the Grignard reagent of formula VI can be employed. Suitable N-protecting groups include alkyl (e.g, methyl), aryl (e.g. phenyl or substituted phenyl), alkyloxyalkyl (e.g., methoxymethyl), benzyloxyalkyl (e.g., benzyloxymethyl), substituted benzyloxyalkyl (e.g, (di-p-methoxyphenyl)methyl), trlphenylmethyl, tetrahydropyranyl, diphenyl phosphinyl, benzene sulfenyl, etc. The N-protecting group can be later removed by conventional means once the Grignard reagent has been reacted with the compound of formula V.

The reaction between compounds of formulae V and VI is generally performed in an inert solvent such as an ether, toluene or tetrahydrofuran. This reaction is performed under the general conditions for a Grignard reaction, e.g., at temperatures of from about 0° C. to about 75° C. The resulting intermediate of formula XVIII

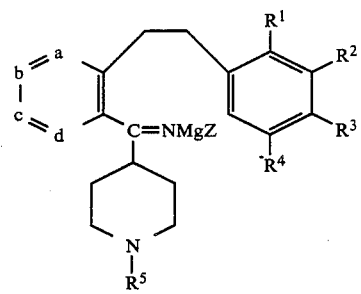

XVIII is hydrolyzed, e.g., with aqueous acid such as aqueous HCl, to prepare the corresponding ketone of formula VII.

The compound of formula VII can be ring-closed to form the desired cycloheptenes ring system by treating the compound VII with a super acid having a Hammett acidity function of less than about minus 12, e.g., minus 13, minus 14, etc. This measure of acidity is defined in Hammett, Louis P., and Deyrup, Alden J., *Journal of the American Chemical Society*, Vol. 54, 1932, p. 2721. Suitable super acids for this purpose include, for example, $HF/BF_3$, $CF_3SO_3H$, $CH_3SO_3H/BF_3$, etc. The reaction can be performed in the absence of or with a suitable inert co-solvent such as $CH_2Cl_2$. The temperature and time of the reaction vary with the acid employed. For example, with $HF/BF_3$ as the super acid system the temperature may be controlled so as to minimize side reactions, such as HF addition to the double bond of the rings. For this purpose, the temperature is generally in the range of from about $+5°$ to $-50°$ C., preferably from about $-30°$ to $-35°$ C. With $CF_3SO_3H$ as the super acid system, the reaction may be run at elevated temperatures, e.g., from about 25° to about 150° C. and at lower temperatures but the reaction then takes longer to complete.

Generally the super acid is employed in excess, preferably in amount of from about 1.5 to about 30 equivalents. For example, with $HF/BF_3$ as the super acid system the volume/weight ratio of HF to the compound of formula VIII in the reaction mixture is preferably from about 30 to about 1.5, more preferably 2.5 to 1.5. In such system, the weight/weight ratio of $BF_3$ to the compound of formula VIII in the reaction mixture is preferably from about 15 to about 0.75, more preferably from about 1 to about 0.75.

If it is desired to proceed via a ketone intermediate of formula XIII

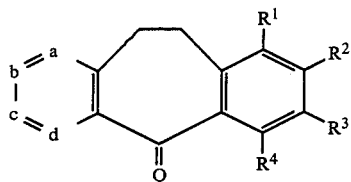

XIII

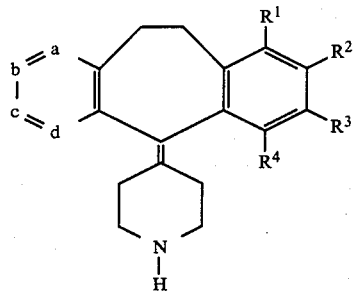

XII a compound of formula IV can be converted directly to a compound of formula XIII by reaction with any of the conventional acidic compounds used for such purpose, e.g., polyphosphoric acid. Alternatively, the compound of formula IV can first be hydrolyzed to the acid form can be prepared from the compounds of formula I or the compounds of formula XI

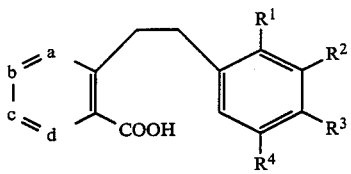

XIV

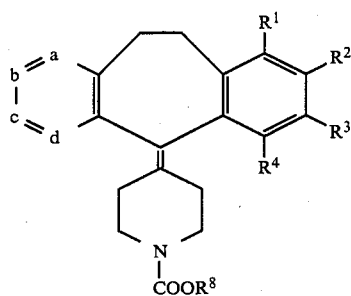

XI e.q., with sulfuric acid. This acid form can then be cyclized, for example, by use of anhydrous HCl gas, oxalyl chloride or thionyl chloride and aluminum chloride. In this latter alternative method, preferably no more than two of $R^1$, $R^2$, $R^3$ and $R^4$ represent a halo, nitro, alkoxy or trifluoromethyl group and more preferably no more than one of $R^1$, $R^2$, $R^3$ and $R^4$ is such a group. Preferably, $R^1$, $R^2$, $R^3$ and $R^4$ are hydrogen in these reactions leading to the compound of formula XIII.

The intermediate of formula XIII above can be reacted with a Grignard reagent to replace the carbonyl group with a piperidylidine or an N-substituted piperidylidene group by processes conventional in the art. Suitable methods are disclosed in U.S. Pat. Nos. 3,326,924, 3,717,647, 4,282,233 and 4,072,756, the disclosures of which are incorporated herein by reference.

The compounds of formula Ia or VIIa wherein $R^7$ is an N-protecting group can be converted to the corresponding 4-piperidylidene (i.e., $R^7$=-H) or 4-($COOR^8$)-piperidylidene (i.e., $R^7$=$COOR^8$) compounds. For example, prior to ring closure of a compound of formula VIIa by reaction with the super acid, e.g. $HF/BF_3$, the $R^7$ N-protecting group can be converted to —H or —$COOR^8$ by any method conventional in the art for such groups. Alternatively, the conversion can take place after ring closure to the compound of formula I. For example, an $R^7$ methoxymethyl group may be converted to -H by treatment with boron trifluoride etherate, acetic anhydride and LiBr, while an $R^7$ benzyloxymethyl group can be converted to -H by catalytic reduction followed by basic hydrolysis. The resulting compounds wherein $R^7$ is —H can be converted to compounds wherein $R^7$ is —$COOR^8$ by reaction with a compound of the formula $ZCOOR^8$ (X) wherein Z is chloro, bromo or iodo. Further, when $R^7$ is an alkyl group, such compounds may be directly converted to compounds wherein $R^7$ is —$COOR^8$ by reaction with a compound $ZCOOR^8$ (X) as described above. Examples of the latter two processes are disclosed in U.S. Pat. No. 4,282,233. Compounds of formula XII Thus, with the compounds of formula XI the $COOR^8$ group can be removed simply by treatment with base. Alternatively, the compounds of formula XII can be prepared by dealkylation of the compounds of formula I wherein $R^5$ is alkyl (preferably methyl), e.g., by reaction with cyanogen bromide and subsequent hydrolysis of the N-cyano product with, for example, aqueous acid solution.

The compounds of formulas I (wherein $R^5$ is alkyl), XI and XII possess desirable pharmacological properties, e.g., antihistaminic and anti-allergy properties and are therefore the desired end products of the process of the invention. Preferred are the compounds wherein d is N; a, b and c are CH; $R^2$ and $R^3$ are each independently selected from hydrogen or halo; and $R^1$ and $R^4$ are hydrogen. In formula I, a preferred $R^5$ N-protecting group is alkyl, preferably methyl, and in formula XI $R^8$ is preferably ethyl. Particularly preferred are the compounds of the formula XIX

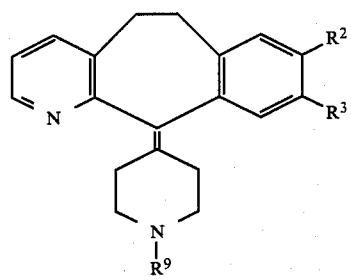

XIX wherein $R^2$=Cl, $R^3$=H and $R^9$=H, $CH_3$ or $COOC_2H_5$; $R^2$=F, $R^3$=H and $R^9$=H, $CH_3$ or $COOC_2H_5$; $R^2$=H, $R^3$=F and $R^9$=H, $CH_3$ or $COOC_2H_5$; $R^2$=$R^3$=F or Cl, and $R^9$=H, $CH_3$ or $COOC_2H_5$; and $R^2$ and $R^3$=H, and $R^9$=$CH_3$.

The following examples are intended to illustrate, but not to limit, the processes and intermediates of the invention.

EXAMPLE 1

Step A: N-(1,1-dimethylethyl)-3-methyl-2-pyridine carboxamide.

2-cyano-3-methyl pyridine (400 g) is suspended in t-BuOH (800 mL) and the mixture heated to 70° C. Concentrated sulphuric acid (400 mL) is added dropwise over 45 minutes. The reaction is complete after a further 30 minutes at 75° C. The mixture is then diluted with water (400 mL), charged with toluene (600 mL) and brought to pH 10 with concentrated aqueous ammonia. The temperature is kept at 50°-55° C. during the work up. The toluene phase is separated, the aqueous layer reextracted and the combined toluene phases are washed with water. Removal of the toluene yields an oil, N-(1,1- dimethylethyl)-3-methyl-2-pyridine carboxamide, from which solid product may crystallize. Product yield of 97% is determined by internal standard assay on gas

Step B: 3-[2-(3-fluoro-phenyl)ethyl]-N-(1,1-dimethylethyl)-2-pyridine carboxamide.

Tetrahydrofuran (125 mL), and N-(1,1- dimethylethyl)-3-methyl-2-pyridine carboxamide (1 equivalent), are charged and cooled to −40° C. under nitrogen. Two equivalents of n-butyllithium are then added over 40 minutes. When half the n-butyllithium is added the mixture turns purple. Sodium bromide (1.3 g) is added and 3-fluoro-benzyl chloride (1.05 equivalents) is added dropwise (1:1 solution in tetrahydrofuran) over 40-50 minutes while the temperature is maintained at −40° C. After 30 minutes at −40° C., the mixture is diluted with water (250 mL) and the organic phase separated. This phase is dried over sodium sulphate and the solvent removed yielding an oil from which solid product, 3-[2-chromatograph. (3-fluoro-phenyl)ethyl]-N-(1,1-dimethylethyl)-2-pyridine carboxamide, may crystallize.

Step C: 3-[2-(3-fluorophenyl)ethyl]-2-pyridinecarbonitrile.

A solution of 3-[2-(3-fluorophenyl)ethyl]-N-(1,1-dimethylethyl)-2-pyridine carboxamide (36.4 g, 0.121 mole) in 123 mL (202.3 g, 1.32 mole) of phosphorous oxychloride is heated at 110° C. for 3.5 hours and stirred at ambient temperature an additional 15 hours. The reaction is quenched with ice and water and the pH of the solution is brought to 8 by the addition of a saturated aqueous solution of potassium carbonate. The product is extracted into ethyl acetate and the solution is concentrated to a residue. Following purification by silica gel chromatography and trituration with pentane, 16.2 g (0.072 mole) of product is obtained in 60% yield.

Step D: (1-methyl-4-piperidinyl)[3-[2-(3fluorophenyl)ethyl]-2-pyridinyl]methanone To a solution of 3-[2-(3-fluorophenyl)ethyl]-2pyridine carbonitrile (28.0 o, 0.123 mole) in 150 mL of dry THF is added 92 mL (1.48 moles/liter, 0.136 mole) of N-methylpiperidyl magnesium chloride over 10 minutes maintaining the temperature at 45°-50° C. The reaction is maintained at 40° C. to 50° C. for another 10 minutes and at ambient temperature for 45 minutes. The reaction is quenched to below pH 2 with aqueous hydrochloric acid and the resulting solution is stirred at 25° C. for 1 hour. The pH of the solution is adjusted to about 8, the oroduct is extracted with ethyl acetate, and the solution is concentrated to a residue. Following purification by silica gel chromatography, 38.3 g of product is obtained as a brown oil.

Sten E: 6,11-dihydro-8-fluoro-11-(1-methyl-4-piperidylidene)-5H-benzo[5,6]cyclohepta[1,2-b]pyridine A solution of (1-methyl-4-piperidinyl)[3-[2-(3fluorophenyl)ethyl]-2-piperidinyl)methanone (15.0 g, 0.046 mole) in 74 mL (125.5 g, 0.837 mole) of trifluoromethanesulfonic acid is stirred at ambient temperature for 18 hours. The reaction is quenched with ice-water and the solution made basic with potassium hydroxide. The product is extracted into ethyl acetate. The ethyl acetate solution is filtered to remove insolubles and the filtrate is concentrated to a residue. Following purification by silica gel chromatography, 5.4 o (0.0175 mole) of oroduct is obtained in 38% yield.

By analogous procedures employing the appropriate substituted benzyl chloride, the corresponding 8-bromo, 9-fluoro, 8,9-dichloro and 9-bromo analogs may be prepared.

EXAMPLE 2

Step B: 3-[2-(3-chlorophenyl)ethyl]-N-(1,1-dimethylethyl)-2-pyridine carboxamide.

31.5 g of N-(1,1-dimethylethyl)-3-methyl-2pyridine carboxamide is dissolved in 600 mL of dry tetrahydrofuran and the resulting solution is cooled to −40° C. Two equivalents of n-butyllithium in hexane are added while the temperature is maintained at −40° C. The solution turned deep purple-red. 1.6 g of sodium bromide is added and the mixture is stirred. A solution of 26.5 g (0.174 mole) m-chlorobenzylchloride in 125 mL of tetrahydrofuran is added while the temperature is maintained at −40° C. The reaction mixture is stirred until the reaction is complete as determined by thin layer chromatography. water is added to the reaction until the color is dissipated. The reaction mixture is extracted with ethyl acetate, washed with water, and concentrated to a residue. A yield of 92% for the product is shown by chromatography.

Step C: 3-[2-(3-chlorophenyl)ethyl]-2-pyridine-carbonitrile

A solution of 3-[2-(3-chlorophenyl)ethyl]-N-(1,1-dimethylethyl)-2-pyridine carboxamide (175 g, 0.544 mole), in 525 mL (863 o, 5.63 mole) of phosphorous oxychloride is heated at reflux for 3 hours. Completion of the reaction is determined by thin laver chromatography. Excess phosphorous oxychloride is removed by distillation at reduced pressure and the residue is quenched into a mixture of water and isopropanol. The pH is brought to 5-7 by addition of 50% aqueous sodium hydroxide solution while maintaining the temperature below 30° C. The crystalline slurry of crude product is filtered and washed with water. Crude product is purified by slurrying the wet cake in hot isopropanol followed by cooling at 0°-5° C. The product is filtered, washed with hexane and dried at below 50° C. Yield: 118 g (HPLC purity 95.7%), m.p. 72°-73° C., 89.4% of theory.

Step D: (1-methyl-4-piperidinyl)[3-[2-(3chlorophenyl)ethyl]-2-pyridinyl]methanone hydrochloride To a solution of oroduct of Step C above (118 g, 0.487 mole) in 1.2 L of dry tetrahydrofuran is added 395 mL (2.48 mole/liter, 0.585 mole, 1.2 eq.) of N- methylpiperidyl magnesium chloride over about 15 minutes maintaining the temperature at 45° C.–50° C. by cooling with water as necessary. The reaction is maintained at 40° C. to 50° C. for about another 30 minutes. Completion of the reaction is determined by thin-layer chromatography. The reaction is quenched to pH below 2 with 2N hydrochloric acid and the resulting solution is stirred at about 25° C. for 1 hour. The bulk of the tetrahydrofuran is removed by distillation and the resulting solution is adjusted to pH 3.5 by the addition of aqueous sodium hydroxide. After cooling to 0° to 5° C., the crystalline hydrochloride salt product is filtered off, washed with ice cold water and dried to constant weight at 60° C. Yield: 168.2 g (HALC purity 94%), m.p. 183°–185° C., 89% of theory. Step E: 8-chloro-6,11-dihydro-11-(1-methyl-piperidylidene)-5H-benzo[5,6]cyclohepta[1,2-b]pyridine To a solution of a product of Step D above (59 g, 0.15 mole) in 120 mL (120 g, 6.0 mole) of hydrofluoric acid at −35° C. is added boron trifluoridine (44.3 g, 0.66 mole) over 1 hour. Completeness of the reaction is determined by thin-layer chromatography. The reaction is quenched using ice, water and potassium hydroxide to a final pH of 10. The product is extracted into toluene and the toluene solution is washed with water and brine. The toluene solution is concentrated to a residue, which is dissolved in hot hexane. Insolubles are removed by filtration and the filtrate is concentrated to an off-white powder. Yield: 45.7 g (HPLC purity: 96%), 92% of theory. Alternative Step E: 8-chloro-6,11-dihydro-11-(1-methyl- piperidylidene)-5H-benzo[5,6]cyclohepta[1,2-b]pyridine A solution of 177 g (0.49 mole) of a product of Step D above in 480 mL (814.1 g, 5.31 mole) of trifluoromethanesulfonic acid at 90°–95° C. for 18 hours under nitrogen. Completeness of the reaction is determined by thin-layer chromatography. The cooled reaction is quenched with ice-water and the pH is adjusted to 6 with barium carbonate. The product is extracted into methylene chloride, which is concentrated under reduced pressure to about 1 liter and washed with water. The product is extracted into 1 N hydrochloric acid, which is treated with 30 g of Darco, and filtered through celite. The pH of the filtrate is adjusted to 10 with 50% aqueous sodium hydroxide and the product is extracted into methylene chloride, which is removed under reduced pressure. The residue is dissolved in hot hexane, which is filtered to remove insolubles. The filtrate is concentrated to a residual beige powder. Yield: 126 g (HPLC purity 80%), 65% of theory.

EXAMPLE 3

Step A: 3-methyl-2-pyridinecarboxamide

A solution of 2-cyano-3-methylpyridine (30.0 g, 0.25 mole) in 500 mL of 6N sodium hydroxide:ethanol (1:1) is stirred at ambient temperature overnight. The product is extracted into ethvl acetate, which is dried (MgSO4) and concentrated to a residue containing 26.6 g (0.19 mole, 76%) of 3-methyl-2-pyridinecarboxamide.
Step B: N-phenyl-3-methyl-2-pyridinecarboxamide To 3-methyl-2-pyridinecarboxamide (15.0 o, 0.11 mole) are added BF3.OEt2 (14.0 mL, 0.11 mole) and tetrahydrofuran (75 mL). After about 5 minutes, aniline (10.3 g, 0.11 mole) is slowly added and the solution is heated at reflux for 5 hours. The reaction is cooled and diluted with water and the oroduct is extracted into ethyl acetate. The solvent is removed and the residue is purified by silica gel chromatography to give 8.32 g (0.39 mole, 35%) of N-phenyl-3-methyl-2-pyridinecarboxamide.

Step C: 3-[2-(3-chlorophenyl)ethyl]-N-(1-phenyl)-2-pyridine carboxamide

To a solution of N-phenyl-3-methyl-2pyridinecarboxamide (1.0 g, 4.71 mmol) in 20 mL of dry tetrahydrofuran at −50° C. is added 2 equivalents of n-butyllithium. Sodium bromide (0.05 g) is added followed by m-chlorobenzyl chloride (0.80 g, 4.95 mmol) dissolved in 3 mL of tetrahydrofuran. The mixture is stirred at −50° C. for 0.5 hour, diluted with water and the organic phase is separated. The solvent is removed under vacuum and the residue is purified by silica gel chromatography yielding 1.14 g (3.38 mmol, 72%) of 3-[2-(3chlorophenyl)ethyl]-N-(1-phenyl)-2-pyridinecarboxamide.

This last compound can be employed in Step C of Example 2 above in place of 3-[2-(3-chlorophenyl)ethyl- N-(1,1-dimethylethyl)-2-pyridine carboxamide to provide the same product, i.e., 3-[2-(3-chlorophenyl)ethyl[-2-pyridine carbonitrile.

EXAMPLE 4

Step A: N-(1,1-dimethylethyl)-3-methyl-2-pyridine carboxamide.

2-cyano-3-methyl pyridine (400g) is suspended in t-butyl alcohol (800 mL) and the mixture heated to 70° C. Concentrated sulphuric acid (400 mL) is added dropwise over 45 minutes. The reaction is complete after a further 30 minutes at 75° C. The mixture is then diluted with water (400 mL), charged with toluene (600 mL) and brought to pH 10 with concentrated aqueous ammonia. The temperature is kept at 50°–55° C. during the work up. The toluene phase is separated, the aqueous layer re-extracted and the combined toluene phases are washed with water. Removal of the toluene yields an oil from which solid product may crystallize. Product yield of 97% determined by internal standard assay on gas chromatograph.

Step B: 3-[2-(phenyl)ethyl]-N-(1,1-dimethylethyl)-2-pyridine carboxamide.

Tetrahydrofuran (125 mL), N-(1,1- dimethylethyl)-3-methyl-2-pyridine carboxamide (1 equivalent) and sodium bromide (1.3 g) are charged and cooled to −40° C. under nitrogen. Two equivalents of nbutyllithium are then added over 40 minutes. When half the n-butyllithium is added the mixture turns purple. Benzyl chloride (1.05 equivalents) is then added dropwise (1:1 solution in tetrahydrofuran) over 40–50 minutes while the temperature is maintained at −40° C. After 30 minutes at −40° C., the mixture is diluted with water (250 ml) and the organic phase separated. This phase is dried over sodium sulphate and the solvent removed yielding an oil from which solid product may crystallize. Product yield of 94% determined by internal standard assay on gas chromatograph.

Step C: Cyclization to 5,6-dihydro-11H-benzo[5,6]cyclohepta[1,2-b]pyridin-11-one Polyphosphoric acid (123.75g) and water (1.25 mL) are heated to 200° C. 3-[2-(phenyl)ethyl]-N-(1,1- dimethylethyl)-2-pyridine carboxamide is then added. After 30 minutes at 200° C. the mixture is allowed to cool. Then the mixture is diluted with water and toluene is added. The mixture is brought to pH 10 with 40% aqueous NaOH. An internal standard assay on gas chromatograph determined a yield of 58% for 5,6-dihydro-11H-benzo-[5,6]cyclohepta[1,2-b]pyridin-11-one. Crystallization of title compound from toluene-hexane gave m.p. 118.5°–119.7° C.

EXAMPLE 5

Step B: 3-[2-(3-chlorophenyl)ethyl]-N-(1,1-dimethylethyl)-2-pyridine carboxamide.

31.5 g of 2-t-butyl-carboxamido-3-methyl pyridine is dissolved in 600 mL of dry tetrahydrofuran and the resulting solution is cooled to −40° C. Two equivalents of n-butyllithium in hexanes are added while the temperature is maintained at −40° C. The solution turned deep purple-red. 1.6 g of sodium bromide is added and the mixture is stirred. A solution of 26.5 g (0.174 mole) m-chlorobenzylchloride in 125 mL of tetrahydrofuran is added while the temperature is maintained at −40° C. The reaction mixture is stirred until the reaction is complete as determined by thin layer chromatography. Water is added to the reaction until the color is dissipated. The reaction mixture is extracted with ethyl acetate, washed with water, and concentrated to a residue. A yield of 92% for the product is shown by chromatography.

Step C: 3-[2-(3-chlorophenyl)ethyl]picolinic acid.

3-[2-(3-chlorophenyl)ethyl]-N-(1,1-dimethylethyl)-2-pyridine carboxamide (1.0 mole, 317 g), sulfuric acid (325 mL) and water (300 mL) are refluxed at about 130° C. for approximately 2 hours. Completeness of the reaction is determined by thin layer chromatography. The reaction mixture is cooled to about 35° C. and added to ice (2 kg). The mixture is then brought to about pH 11 with 50% sodium hydroxide. Additional ice (1 kg) is added, followed by ethyl acetate (1 liter) and hexane (525 mL). The mixture is acidified to about pH 4 with sulfuric acid and stirred for about 1 hour. Crude product is isolated by filtration, washed with water and hexane and optionally dried at about 50° C. Then the crude product is dissolved in ethyl acetate by refluxing at about 75° C. After treating the solution with decolorizing carbon (5 g), the filtrate is concentrated and cooled to about 15° C. Purified product is isolated by filtration, washed with hexane: ethyl acetate (3:1) and dried at about 50° C. A second crop may be obtained by concentrating the mother liquor and recrystallizing from ethyl acetate as described above. The yield of product is shown to be 60%.

Step D: Cyclization to 8-chloro-5,6-dihydro-11H-benzo[5,6]cyclohepta[1,2-b]pyridin-11-one A stream of anhydrous HCl gas is passed into a suspension of 3-[2-(3-chlorophenyl)ethyl]picolinic acid (0.5 mole) and tetrachloroethane (1500 mL) maintained by cooling at about 25° C. After about 1 hour, 64 mL of oxalyl chloride is added. A slight stream of HCl is passed through the mixture for 25 hours. Completion of the reaction is checked by thin layer chromatography. The reaction is then cooled in an ice bath to about 5° C. and with stirring 1 mole of AlCl3 is added in about 1 hour. The reaction mixture is kept at ice bath temperature for 22 hours. Then another 0.25 mole of AlCl3 is added and the reaction is continued for another 3 hours. After this 870 mL of 3.5% aqueous HCl is added to the reaction mixture at below 25° C. The bottom oil layer is separated and re-extracted with 3×400 mL of 3.5% aq. HCl. The combined water layers are washed with 2×200 mL of ether.

Added to the water layer are 1300 mL of benzene and 100 g of supergel. This is followed with a simultaneous addition of 480 mL of 50% aqueous NaOH and 2 kg of ice to maintain the temperature at 20°–25° C. the cake is filtered and washed with 2×180 mL of toluene. The two layers of filtrate are separated and the water layers are re-extracted with 2×260 mL of toluene.

The combined toluene layers are washed with 200 mL of 5% aqueous NaHCO3, 2×250 mL of 20% aqueous NaCl, dried over Na2SO4 and simultaneously treated with 5 g of Darco. The solution is filtered and the solvent is removed leaving light tan solids of title product, m.p. 99°–101° C., yield 79%.

EXAMPLE 6

Ethyl chloroformate (8.5 mL, 9.65 g, 0.089 mole) is slowly added at 80° C. to a solution of 8-fluoro11-(1-methyl-4-piperidylidene)-6,11-dihydro-5H-benzo[5,6]cyclohepta[1,2-b]pyridine (5.4 g, 0.0175 mole) and triethylamine (3.6 mL, 2.61 g, 0.026 mole) in 60 mL of toluene. Following complete addition, the temperature is maintained at 80° C. for 1 hour. The reaction mixture is treated with charcoal, filtered, and concentrated to a residue. Following purification by silica gel chromatography and crystallization from pentane, 4.10 g (0.011 mole) of 8-fluoro-6,11-dihydro-11-(1- ethoxycarbonyl-4-piperidylidene)-5H-benzo[5,6]cyclohepta[1,2-b]pyridine is obtained in 63% yield. 8-bromo, 8,9-dichloro, 9-chloro, and 9-fluoro analogs of this 8-fluoro-11-(1-ethoxycarbonyl-4piperidylidene) compound can be prepared.

EXAMPLE 7

A solution of 8-fluoro-6,11-dihydro-11-(1- ethoxycarbonyl-4-piperidylidene)-5H-benzo[5,6]cyclohepta[1,2-b]pyridine (3.6 g, 0.0098 mole) and potassium hydroxide (4.5 g, 0.094 mole) in 50 mL of ethanol:water (1:1) is heated at reflux for 66 hours. The reaction mixture is diluted with brine and the product is extracted into ethyl acetate. The solution is concentrated to a residual solid which is washed with acetone/ethyl acetate to yield 2.76 g (0.0094 mole) of 8- fluoro-11-(4-piperidylidene)-6,11-dihydro-5H-benzo[5,6]cyclohepta[1,2-b]pyridine.

By analogous procedures, the corresponding 8-chloro, 8-bromo, 8,9-dichloro, 9-chloro and 9-fluoro analogs of this 8-fluoro-11-(4-piperidylidene) compound can be prepared.

EXAMPLE 8

A solution of (1-ethoxycarbonyl-4piperidinyl)[3-[2-(3-chlorophenyl)ethyl]-2pyridinyl]methanone hydrochloride (0.5 g, 1.25 mmol) (prepared by reacting the corresponding 1-methyl-H-piperidinyl compound with ethyl chloroformate) in 1.5 mL of trifluoromethane sulfonic acid is stirred at ambient temperature for 24 hours. The reaction is diluted with ice and water, neutralized with barium carbonate, and the product extracted into ethyl acetate. The solvent is removed and following purification of the residue by silica gel chromatography, 8-chloro-6,11-dihydro-11-(1- ethoxycarbonyl-4-piperidylidene)-5H-benzo[5,6]cyclohepta[1,2-b]pyridine is obtained.

The compound 8-chloro-6,11-dihydro-11-(4-piperidylidene)-5H-benzo[5,6]cyclohepta[1,2-b]pyridine can be prepared by the above method by substituting (4-piperidinyl)[3-[2-(3-chlorophenyl)ethyl]-2-pyridinyl]methanone in place of the (1-ethoxycarbonyl-4-piperidylidene)[3-[2-(3-chlorophenyl)ethyl]-2pyridinyl]methanone hydrochloride.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A compound of the formula IV

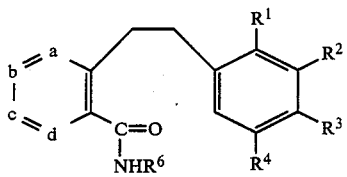

IV wherein:

a, b, c and d represent CH or one of a, b, c and d represents N and the others represent CH;

$R^1$, $R^2$, $R^3$ and $R^4$ may be the same or different and each independently represents hydrogen, alkyl having from 1 to 6 carbon atoms, halogen, nitro, alkoxy having from 1 to 6 carbon atoms or trifluoromethyl; and $R^6$ represents a tertiary butyl group.

2. A compound according to claim 1, wherein $R^2$ and $R^3$ may be the same or different and each is selected from hydrogen or halo; $R^1$ and $R^4$ are hydrogen; d is N; and a, b, and c are CH.

3. A compound according to claim 1, wherein $R^2$ is H, chloro or fluoro; $R^1$, $R^3$ and $R^4$ are hydrogen; d is N; and a, b, and c are CH.

4. A compound according to claim 3, wherein $R^2$ is chloro.

5. A compound according to claim 3, wherein $R^2$ is H.

6. A compound of the formula XV

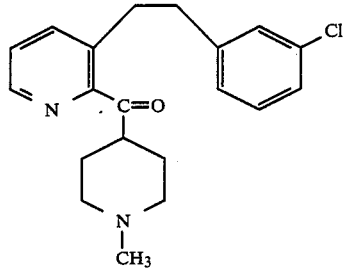

XV or an acid addition salt thereof.

7. A compound according to claim 6, which is the hydrochloride salt thereof.

* * * * *